US008901351B2

(12) United States Patent
Amao et al.

(10) Patent No.: US 8,901,351 B2
(45) Date of Patent: Dec. 2, 2014

(54) PRECURSOR OF POLYMERIZABLE COMPOUND

(71) Applicant: FUJIFILM Corporation, Tokyo (JP)

(72) Inventors: Akihito Amao, Kanagawa (JP); Hirotaka Kitagawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/774,936

(22) Filed: Feb. 22, 2013

(65) Prior Publication Data

US 2013/0296606 A1    Nov. 7, 2013

(30) Foreign Application Priority Data

Mar. 22, 2012   (JP) ................. 2012-065144

(51) Int. Cl.
*C07C 233/18* (2006.01)
*C07C 233/05* (2006.01)
*C07C 231/12* (2006.01)

(52) U.S. Cl.
CPC ............. *C07C 233/18* (2013.01); *C07C 231/12* (2013.01)
USPC ....................................... 564/153

(58) Field of Classification Search
CPC ............................ C07C 233/05; C07C 233/18
USPC ....................................... 564/153
See application file for complete search history.

(56) References Cited

U.S. PATENT DOCUMENTS

| | | | |
|---|---|---|---|
| 2,683,741 A | 7/1954 | Wiley | |
| 3,641,116 A | 2/1972 | Froehlich | |
| 4,914,225 A | 4/1990 | Suzuki et al. | |
| 2002/0160964 A1 | 10/2002 | Jack et al. | |
| 2011/0205291 A1 | 8/2011 | Yasuda et al. | |

FOREIGN PATENT DOCUMENTS

| | | |
|---|---|---|
| DE | 743466 C | 11/1952 |
| JP | S63-045245 A | 2/1988 |
| JP | 04-208258 A | 7/1992 |
| JP | 2003-521461 A | 7/2003 |
| JP | 2005-307198 A | 11/2005 |
| JP | 2007-031372 A | 2/2007 |
| JP | 2010-079085 A | 4/2010 |
| JP | 2010-274476 A | 12/2010 |
| JP | 2011-195822 A | 10/2011 |
| JP | 2012-206992 A | 10/2012 |
| WO | 2006/055437 A2 | 5/2006 |
| WO | 2012/133182 A1 | 10/2012 |

OTHER PUBLICATIONS

The extended European search report issued on Aug. 6, 2013, which corresponds to EP13156109.4 and is related to U.S.Appl. No. 13/774,936.
B.J. Ludwig et al., : "Carbamate Derivatives Related to Meprobamate", Journal of Medicinal Chemistry, vol. 12, No. 3, May 1, 1969, pp. 462-472.
W.D.Roll, : "Synthesis of N,N'-Haloacyl Analogs of p,p'-Oxydianiline as Potential Antineoplastic Agents", Journal of Pharmaceutical Sciences, vol. 55, No. 10, Oct. 1966, pp. 1151-1152.
E. Terreno et al., : "Highly shifted LIPOCEST agents based on the encapsulation of neutral polynuclear paramagnetic shift reagents", Chemical Communications, vol. 8, No. 5, Nov. 26, 2007, pp. 600-602.
T.A. Andreyanova et al., : "Synthesis and Antitumor Activity of Diazepine Derivatives and Their Structural Analogs", Pharmaceutical Chemistry Journal, vol. 32, No. 7, Jul. 1998, pp. 352-355.
A. Senning et al., : "Neue Bis-sulfonsäureester mit zytostatischer Wirkung", Arzneimittel Forschung. Drug Research, ECV Editio Cantor Verlag, Auledorf, DE, vol. 26, No. 10, 1976, pp. 1800-1809.
An Office Action; "Notice of Reasons for Rejection," issued by the Japanese Patent Office on Apr. 1, 2014, which corresponds to Japanese Patent Application No. 2012-065144 and is related to U.S. Appl. No. 13/774,936; with English language translation.

*Primary Examiner* — Shailendra Kumar
(74) *Attorney, Agent, or Firm* — Studebaker & Brackett PC (57) ABSTRACT

A compound represented by formula (I):

Formula (I)

$$X-CH_2-CH(R)-\overset{O}{\overset{\|}{C}}-N(Ra)-Z-(L-N(Ra)-\overset{O}{\overset{\|}{C}}-CH(R)-CH_2-X)_n$$

wherein, in formula (I), R represents a hydrogen atom or an alkyl group having 1 to 4 carbon atom(s); Ra represents a hydrogen atom, an alkyl group, an aryl group, or a heterocyclic group; X represents a halogen atom, or an alkyl- or aryl-sulfonyloxy group; L represents a divalent linking group; Z represents a (n+1)-valent organic group; and n represents an integer of 1 to 6, a plurality of Rs and Ras and Xs may be the same or different from each other, respectively, and when n represents 2 to 6, a plurality of Ls may be the same or different from each other.

3 Claims, 5 Drawing Sheets

PRECURSOR OF POLYMERIZABLE COMPOUND

FIELD OF THE INVENTION

The present invention relates to a compound which is a precursor of a polymerizable compound.

BACKGROUND OF THE INVENTION (Meth)acrylamides are polymerizable compounds showing high reactivity. These compounds are widely utilized as a raw material or a crosslinking agent of various kinds of synthetic resins in an industrial application such as a coating material, paint, printing ink, an adhesive, and a resist material. For example, an ink composition containing the (meth)acrylamides as a radical polymerizable compound is described in JP-A-2005-307198 ("JP-A" means unexamined published Japanese patent application).

The (meth)acrylamides are generally obtained by reacting an amine compound with a (meth)acrylate. However, the method results in low yield because an alkylamine compound further reacts with a (meth)acrylic group of an amidated compound thus obtained, or this is further amidated.

Further, methods for producing (meth)acrylamides by reacting an alkylamine with an alkyl acid alkyl to convert them into an aminoamide (amide adduct), and thermally decomposing the resultant or adjusting a concentration of a monoalkylamine are known (for example, JP-A-4-208258 and U.S. Pat. No. 2,683,741). However, these methods still have a problem of suppressing by-products when a plurality of (meth)acrylamide groups are included in one molecule.

Under the circumstances, a novel precursor (synthetic intermediate) for efficiently producing a compound that has a plurality of (meth)acrylamide groups and that is useful for the raw material or the crosslinking agent for various kinds of synthetic resins, particularly the ink composition, has been desired.

SUMMARY OF THE INVENTION

The present invention resides in a compound represented by formula (I):

Formula (I)

wherein, in formula (I), R represents a hydrogen atom or an alkyl group having 1 to 4 carbon atom(s); Ra represents a hydrogen atom, an alkyl group, an aryl group, or a heterocyclic group; X represents a halogen atom, or an alkyl- or aryl-sulfonyloxy group; L represents a divalent linking group; Z represents a (n+1)-valent organic group; and n represents an integer of 1 to 6, a plurality of Rs and Ras and Xs may be the same or different from each other, respectively, and when n represents 2 to 6, a plurality of Ls may be the same or different from each other.

Other and further features and advantages of the invention will appear more fully from the following description, appropriately referring to the accompanying drawings.

DETAILED DESCRIPTION OF THE INVENTION

The present inventors have found that a compound having a specific partial structure can be used as a synthetic precursor of a polymerizable compound such as a (meth)acrylamide compound, and that a higher yield can be achieved according to a synthetic method through the precursor, as compared with the conventional method. The present invention has been completed based on the finding.

According to the present invention, there is provided the following means:

<1> A compound represented by formula (I):

Formula (I)

wherein, in formula (I), R represents a hydrogen atom or an alkyl group having 1 to 4 carbon atom(s); Ra represents a hydrogen atom, an alkyl group, an aryl group, or a heterocyclic group; X represents a halogen atom, or an alkyl- or aryl-sulfonyloxy group; L represents a divalent linking group; Z represents a (n+1)-valent organic group; and n represents an integer of 1 to 6, a plurality of Rs and Ras and Xs may be the same or different from each other, respectively, and when n represents 2 to 6, a plurality of Ls may be the same or different from each other.

<2> The compound according to the item <1>, wherein n is 3 to 6.

<3> The compound according to the item <1> or <2>, wherein L at least contains a group selected from —O—, an alkylene group, and a group obtained by combining these groups.

<4> The compound according to any one of the items <1> to <3>, wherein the compound represented by formula (I) is a compound represented by formula (II):

Formula (II)

wherein, in formula (II), Rb represents a hydrogen atom, an alkyl group, or -L-N(Ra)—C(=O)—CH(R)—CH$_2$—X; and R, Ra, X and L have the same meanings as those of formula (I).

<5> The compound according to any one of the items <1> to <4>, wherein the compound represented by formula (I) is a compound represented by formula (III):

Formula (III)

wherein, in formula (III), R, Ra, X and L have the same meanings as those of formula (I).
<6> The compound according to any one of the items <1> to <5>, wherein the compound represented by formula (I) is a compound represented by formula (1):

Formula (1)

wherein, in formula (1), $R^1$ represents a hydrogen atom or a methyl group; $X^1$ represents a halogen atom; $L^1$ represents a divalent linking group; $L^2$ represents a straight or branched alkylene group having 2 to 4 carbon atoms, and $L^2$ is linked to adjacent groups through at least two carbon atoms; k represents 2 or 3; m represents an integer of 0 to 6; and a plurality of $R^1$, $L^1$s, $L^2$s, $X^1$s, ks and ms may be the same or different from each other, respectively.
<7> The compound according to any one of the items <1> to <6>, wherein the compound is a synthetic intermediate of a (meth)acrylamide compound represented by formula (A):

Formula (A)

wherein, in formula (A), R represents a hydrogen atom or an alkyl group having 1 to 4 carbon atom(s); Ra represents a hydrogen atom, an alkyl group, an aryl group, or a heterocyclic group; L represents a divalent linking group; Z represents a (n+1)-valent organic group; and n represents an integer of 1 to 6, a plurality of Rs and Ras may be the same or different from each other, respectively, and when n represents 2 to 6, a plurality of Ls may be the same or different from each other.

In the present invention, the term "(meth)acrylamide(s)" means acrylamide(s) and/or methacrylamide(s). Further, in the present invention, "to" denotes a range including numerical values described before and after it as a minimum value and a maximum value.

[Precursor Compound]

The present invention has been made based on a finding that a compound including at least the following partial structure (I) or (II) can be used as an intermediate or precursor for synthesizing a polymerizable compound such as a (meth)acrylamide compound.

Partial structure (I)

Partial structure (II)

In the partial structure (I) and (II), R represents a hydrogen atom or an alkyl group having 1 to 4 carbon atom(s); X represents a halogen atom, or an alkyl- or aryl-sulfonyloxy group; and * represents a linking site in a precursor compound.

The compound of the present invention is represented by the following formula (I), and can be used as the precursor (synthetic intermediate) for synthesizing the polymerizable compound such as the (meth)acrylamide compound.

Formula (I)

In formula (I), R represents a hydrogen atom or an alkyl group having 1 to 4 carbon atom(s); Ra represents a hydrogen atom, an alkyl group, an aryl group, or a heterocyclic group; X represents a halogen atom, or an alkyl- or aryl-sulfonyloxy group; L represents a divalent linking group; Z represents a (n+1)-valent organic group; and n represents an integer of 1 to 6, a plurality of Rs and Ras and Xs may be the same or different from each other, respectively, and when n represents 2 to 6, a plurality of Ls may be the same or different from each other.

R is preferably a hydrogen atom or a methyl group, and more preferably a hydrogen atom.

Ra is preferably a hydrogen atom or an alkyl group, more preferably a hydrogen atom or an unsubstituted alkyl group, and furthermore preferably a hydrogen atom.

The alkyl group represented by Ra is preferably a straight or branched chain alkyl group having 1 to 8 carbon atom(s), for example, methyl, ethyl, isopropyl, tert-butyl, and 2-ethylhexyl.

The aryl group represented by Ra is preferably an aryl group having 6 to 14 carbon atoms, for example, a phenyl group and a naphthyl group.

The heterocyclic group represented by Ra includes an aromatic heterocyclic group or a non-aromatic heterocyclic group, and also includes a single ring or a condensed ring. The heterocyclic group preferably includes a hetero atom selected from an oxygen atom, a sulfur atom and a nitrogen atom as an annular atom, and the heterocyclic group is preferably a 5-membered or a 6-membered ring. The specific example of heterocycle of the heterocyclic group include a pyrrole ring, a imidazole ring, a pyrazole ring, a pyridine ring, a triazine ring, an indole ring, a thiophene ring, a furan ring, a piperazine ring, a piperidine ring, and a morpholine ring.

X is preferably a halogen atom (for example, an iodine atom, a bromine atom, or a chlorine atom), an alkylsulfonyloxy group (preferably, an alkylsulfonyloxy group having 1 to 8 carbon atom(s), for example, methanesulfonyloxy, ethanesulfonyloxy, or octanesulfonyloxy), or an arylsulfonyloxy group (preferably, an arylsulfonyloxy group having 6 to 12 carbon atoms, for example, benzenesulfonyloxy or toluenesulfonyloxy). X is preferably a halogen atom, more preferably an iodine atom, a bromine atom, or a chlorine atom, and particularly preferably a chlorine atom.

L represents a linking group, but includes no single bond. That is, L represents a divalent linking group.

L is preferably an alkylene group, an ethynylene group, an arylene group, a divalent heterocyclic group, —O—, —S—, —N(Ra)—, —C(=O)—, —SO—, or —SO$_2$—, or a group obtained by combining these (for example, -alkylene-O—, —O—C(=O)—, —C(=O)—O—, —C(=O)—N(Ra)—, —N(Ra)—C(=O)—, —SO$_2$—N(Ra)—, or —N(Ra)—SO$_2$—). More preferably, L is a linking group which at least contains a group selected from —O—, an alkylene group, and a group obtained by combining these groups, as a partial structure. Further preferably, L consists of a group selected from —O—, an alkylene group, and a group obtained by combining these groups.

These groups may have a substituent. The substituent is preferably an alkyl group, an aryl group, or a hydroxyl group.

Specific examples of the above-described alkylene group include methylene, ethylene, propylene, butylene, pentylene, hexylene, heptylene, octylene, and nonylene.

Specific examples of the above-described arylene group include phenylene and naphthylene.

A heterocycle in the above-described divalent heterocyclic group includes an aromatic heterocycle or a non-aromatic heterocycle, and also includes a single ring or a condensed ring. The heterocycle preferably includes a hetero atom selected from an oxygen atom, a sulfur atom and a nitrogen atom as an annular atom, and the heterocycle is preferably a 5-membered or 6-membered ring. Specific examples of such a heterocycle include a pyridine ring, a pyrazine ring, a pyrimidine ring, a pyridazine ring, a triazine ring, a quinoline ring, an isoquinoline ring, a quinazoline ring, a cinnoline ring, a phthalazine ring, a quinoxaline ring, a pyrrole ring, an indole ring, a furan ring, a benzofuran ring, a thiophene ring, a benzothiophene ring, a pyrazole ring, an imidazole ring, a benzimidazole ring, a triazole ring, an oxazole ring, a benzoxazole ring, a thiazole ring, a benzothiazole ring, an isothiazole ring, a benzisothiazole ring, a thiadiazole ring, an isoxazol ring, a benzisoxazole ring, a pyrrolidine ring, a piperidine ring, a piperazine ring, an imidazolidine ring, and a thiazoline ring. In addition, according to the above-described specific examples, the heterocycle is shown in the form of a heterocycle in which two bonding positions are omitted, but the two bonding positions are not limited. For example, the pyridine ring may be bonded on two positions of any of 2-position to 6-position, to be pyridine-2,4-diyl or pyridine-2,6-diyl. Replacement on 3-position or 4-position is allowed.

Among the divalent heterocyclic groups, a divalent aromatic heterocyclic group is preferable. A heterocycle of the divalent aromatic heterocyclic group is preferably a pyridine ring, a pyrazine ring, a pyrimidine ring, a pyridazine ring, a triazine ring, a pyrazole ring, an imidazole ring, a benzimidazole ring, a triazole ring, a thiazole ring, a benzothiazole ring, an isothiazole ring, a benzisothiazole ring, or a thiadiazole ring. These heterocycles may have a substituent. Specific examples of the substituent include an alkyl group, an aryl group, and an alkoxy group.

Z represents a (n+1)-valent organic group, and n represents 1 to 6.

n is preferably 2 to 6, more preferably 3 to 6, and particularly preferably 3.

Z is preferably a (n+1)-valent aliphatic group, and more preferably a (n+1)-valent alkyl group. Z preferably having 1 to 10 carbon atom(s), more preferably 1 to 8, further preferably 1 to 4, and particularly preferably 1. When Z has one carbon atom, Z is represented in the form of >C<.

The compound represented by formula (I) is preferably a compound represented by the following formula (II).

Formula (II)

In formula (II), Rb represents a hydrogen atom, an alkyl group, or -L-N(Ra)—C(=O)—CH(R)—CH$_2$—X. R, Ra, X and L have the same meanings as those of the above formula (I).

As an alkyl group in Rb, an alkyl group having 1 to 10 carbon atom(s) is preferable, and the alkyl group may have a substituent. Specific examples of such a substituent include an alkyl group, an alkenyl group, an aryl group, a heterocyclic group, a halogen atom, a hydroxyl group, an alkoxy group, an aryloxy groups, an alkylthio group, an arylthio group, an amino group, an alkylamino group, an arylamino group, a heterocyclic amino group, an acyl group, an alkyloxycarbonyl or aryloxycarbonyl group, an acyloxy group, an acylamino group, an alkylsulfonyl or arylsulfonyl group, an alkylsulfonamide or arylsulfonamide group, a carbamoyl group, a sulfamoyl group, and a cyano group.

Rb is preferably -L-N(Ra)—C(=O)—CH(R)—CH$_2$—X. In this case, the formula (II) is represented by the following formula (III).

Formula (III)

In formula (III), R, Ra, X and L have the same meanings as those of the formula (I), and the preferable range thereof are also the same as those of the formula (I).

In the present invention, the compound represented by any one of the formulae (I) to (III) is particularly preferably a compound represented the following formula (1).

A plurality of ms may be the same or different from each other, and they are preferably the same.

The compound represented by formulae (1) is particularly preferably a compound represented the following formula (2).

Formula (1)

In formula (1), $R^1$ represents a hydrogen atom or a methyl group; $X^1$ represents a halogen atom; $L^1$ represents a divalent linking group; $L^2$ represents a straight or branched alkylene group having 2 to 4 carbon atoms, and $L^2$ is linked to adjacent groups through at least two carbon atoms; k represents 2 or 3; m represents an integer of 0 to 6; and a plurality of $R^1$s, $L^1$s, $L^2$s, $X^1$s, ks and ms may be the same or different from each other, respectively.

The divalent linking group of $L^1$ is preferably the divalent linking group as described in L.

Among the alkylene group exemplified in L, $L^1$ is preferably the alkylene group having 1 to 6 carbon atom(s), more preferably 1 to 3 carbons atom(s), and particularly preferably 1 carbon atom.

Among the arylene group exemplified in L, $L^1$ is preferably the arylene group having 6 to 14 carbon atoms, more preferably 6 to 10 carbons atoms, and particularly preferably 6 carbon atoms. The arylene group may have a substituent. Specific examples of the substituent include an alkyl group and an alkoxy group.

Among the divalent heterocyclic group exemplified in L, the preferable divalent heterocyclic group of $L^1$ is the same as those of L.

Among the above groups, $L^1$ is preferably an alkylene group.

In formula (1), k represents 2 or 3. A plurality of ks may be the same or different from each other, and they are preferably the same. $C_kH_{2k}$ may be a straight chain structure or a branched chain structure.

In formula (1), m represents an integer of 0 to 6. m is preferably an integer of 0 to 5, and more preferably 0 to 3.

Formula (2)

In formula (2), $R^1$ and $X^1$ have the same meanings as those of $R^1$ and $X^1$ in formula (1), and the preferable range of $R^1$ and $X^1$ are also the same as those of $R^1$ and $X^1$ in formula (1). A plurality of $R^1$s and $X^1$s may be the same or different from each other, and they are preferably the same.

Hereinafter, specific example of the compound represented by formula (I) in the present invention, but the present invention is not limited thereto.

(1)

(2)

(3)

(4)

(5)

(6)

(7)

(8)

(9)

(10)

(11)

(12)

(13)

(14)

(15)

(16)

[Synthetic Method of the Precursor Compound]

A compound including the above-described partial structure (I) or (II) can be synthesized, for example, by using an amine compound exemplified below as a raw material and applying the following synthetic methods 1 to 3.

Synthetic Method 1

A method in which an amine compound is allowed to react with an acid halide compound in the presence of a base.

Synthetic Method 2

A method in which an amine compound is allowed to react with a carboxylic acid compound and a condensing agent in the presence of a base.

Synthetic Method 3

A method for synthesizing the precursor compound according to an ester-amide exchange reaction by heating an amine compound and an ester compound.

In the amine compound exemplified above, Ph represents a phenyl group and Me represents a methyl group, respectively.

Further, other amine compounds can be used, for example, an amine compound as described in databases, such as Chemical Abstracts and CAS, an amine compound as described in books, such as Aldrich Structure Index, 1996-1997 ed., an amine compound available from a reagent manufacturer brochure. Moreover, even an amine compound that is not described in the above-described databases, books, or the like can be synthesized according to a generally known reaction (for example, a substitution reaction of amine; a reduction reaction of nitro, azide, or nitrile; a hydrolysis reaction of amide, imine, or isocyanate) by using a compound that can be a synthetic precursor of the amine compound.

Specific examples of the method for synthesizing the compound represented by the formula (I) include the following general synthetic methods using an amine compound as a starting material.

Synthetic Method 1

A method in which an amine compound is allowed to react with an acid halide compound in the presence of a base.

Synthetic Method 2

A method in which an amine compound is allowed to react with a carboxylic acid compound and a condensing agent in the presence of a base.

Synthetic Method 3

A method for synthesizing the precursor compound according to an ester-amide exchange reaction by heating an amine compound and an ester compound.

These reactions can be performed according to a method described in Shin Jikken Kagaku Koza (New Experimental Chemistry Course) 14, Synthesis and Reaction of Organic Compounds (V), 11.6: Protection of Amino Groups, pp. 2555 to 2569.

Examples of an amine compound used in the above-described synthetic method include the following compounds.

-continued

These amine compound may be used from a commercial product, or may be synthesized according to the generally known reaction (for example, the substitution reaction of amine; the reduction reaction of nitro, azide, or nitrile; the hydrolysis reaction of amide, imine, or isocyanate) by using the compound that can be the synthetic precursor of the amine compound.

In particular, amino alcohols having an amino group and a hydroxyl group can be converted into —OCH$_2$(CR$^1$)CH$_2$NH$_2$ (herein, R$^1$ represents a hydrogen atom or a methyl group.) by converting —OH as a hydroxyl group into —OCH$_2$(CR$^1$)CN with (meth)acrylonitrile, and then reducing the nitrile group. In a similar way, HN(Ra)—Z-[L-N(Ra)]$_n$ can be easily synthesized (herein, Ra, L, Z, and n have the same meanings as those of formula (I).).

Representative examples are shown hereinafter.

[Method for Synthesizing a (Meth)Acrylamide Compound Using a Precursor Compound]

The compound represented by formula (I) according to the present invention can be used as a precursor for synthesizing a (meth)acrylamide compound represented by formula (A).

Formula (A)

In formula (A), R represents a hydrogen atom or an alkyl group having 1 to 4 carbon atom(s); Ra represents a hydrogen atom, an alkyl group, an aryl group, or a heterocyclic group; L represents a divalent linking group; Z represents a (n+1)-valent organic group; and n represents an integer of 1 to 6, a plurality of Rs and Ras may be the same or different from each other, respectively, and when n represents 2 to 6, a plurality of Ls may be the same or different from each other.

In synthesis of the (meth)acrylamide compound using the precursor compound of the present invention, for example, the (meth)acrylamide compound can be obtained by allowing a base (an organic base and/or an inorganic base) to act on the precursor compound of the present invention, and forming a carbon-to-carbon double bond at a terminal according to an elimination reaction between X$^1$ of the precursor and a hydrogen atom bound to the carbon atom to which R$^1$ is bonded.

In the following synthetic scheme, a specific example of a method is shown for synthesizing a precursor compound of the present invention [a compound represented by formula (2) in the following scheme] from an amine compound, and further synthesizing a (meth)acrylamide compound 1 from the precursor. In addition, R$^1$ and X$^1$ in the following synthetic scheme have the same meanings as those of R$^1$ and X$^1$ in formula (2) as described above.

Synthetic scheme

(A)

(B)

(C)

Formula (2)

(Meth)acrylamide compound 1

According to the above synthetic scheme, first, tris(hydroxymethyl)aminomethane is used as a starting material (A) to allow a hydroxyl group of tris(hydroxymethyl)aminomethane to react with acrylonitrile or methacrylonitrile, and thus a (meth)acrylonitrile adduct is obtained as an intermediate (B). Next, the intermediate (B) obtained is allowed to react with hydrogen in the presence of a catalyst, and thus an amine form as an intermediate (C) is obtained according to a hydrogenation reaction. The intermediate (C) obtained is further allowed to react with 3-chloropropionic acid chloride or 3-chloro-2-methylpropionic acid chloride to perform amidation, and thus a compound represented by formula (2) as a precursor compound of the present invention can be obtained. As an amidating agent, di 3-chloropropionic anhydride or di 3-chloro-2-methylpropionic acid anhydride may be used in place of the above acid chloride. When both 3-chloropropionic acid chloride and 3-chloro-2-methylpropionic acid chloride are used in the above amidation process, a compound represented by formula (2) having both a 3-chloropropionic acid amide group and a 3-chloro-2-methylpropionic acid amide group in the same molecule can be obtained as a final product. Finally, the (meth)acrylamide compound 1 can be derived from the compound represented by formula (2) by allowing a base to act on the compound.

In the above synthetic scheme, the process from (A) to (B) is preferably performed at 0 to 60° C. for 30 minutes to 8 hours, the process from (B) to (C) is preferably performed at 20 to 45° C. for 2 hours to 16 hours, the process from (C) to the compound represented by formula (2) is preferably performed at 0 to 30° C. for 30 minutes to 6 hours, and a process for synthesizing the (meth)acrylamide compound 1 from the compound represented by formula (2) is preferably performed at 0° C. to 60° C. for 1 hour to 12 hours.

The precursor compound of the present invention and the (meth)acrylamide compound as the final compound can be isolated and collected from a reaction production mixture according to an ordinary method. The compounds can be isolated, for example, by extraction with an organic solvent, crystallization using a poor solvent, column chromatography using silica gel.

The precursor compound of the present invention can be easily converted into the polymerizable compound such as the (meth)acrylamide compound. According to a synthetic reaction of the (meth)acrylamide compound through the precursor compound of the present invention as the synthetic intermediate as shown in the above-described synthetic scheme, the (meth)acrylamide compound as the final product can be obtained with a high yield. The synthetic reaction through the precursor compound of the present invention as the intermediate can produce the (meth)acrylamide compound with a high yield, as compared with a general synthetic method in which the (meth)acrylamide compound is synthesized by allowing (meth)acrylic acid chloride or (meth)acrylic anhydride to react with an amine compound under basic conditions.

The polymerizable compound such as the (meth)acrylamide compound as obtained by the precursor compound of the present invention polymerizes by light or heat to show hardening properties. Therefore, the polymerizable compound can be used in various applications as a radical polymerizable compound.

In particular, the compound represented by the formula (A) as obtained by the compound represented by formula (I) of the present invention is useful as a crosslinking agent or a curing agent for a photosensitive resin composition or inkjet ink. For example, when the polymerizable compound is used in Examples as described in JP-A-2011-214001, JP-A-2011-248354, or JP-A-2012-32556, an effect as described in these documents is exhibited.

According to the present invention, it is possible to provide a compound useful as a precursor for synthesizing a polymerizable compound such as a (meth)acrylamide compound.

The present invention will be described in more detail based on the following examples, but the invention is not intended to be limited thereto. In the following Examples, the terms "part" and "%" with respect to the composition are values by mass, unless they are indicated differently in particular.

EXAMPLES

Example 1

A compound in which $R^1$ is H, and $X^1$ is Cl (chlorine atom) in the formula (2) was synthesized as follows. Hereinafter, the compound is referred to as an exemplified compound (1).

Exemplified compound (1)

Synthesis of Exemplified Compound (1)
(First Step)
To a 1 L volume three-necked flask equipped with a stirrer bar, 121 g (1 equivalent) of tris(hydroxymethyl)aminomethane (A) (made by Tokyo Chemical Industry Co., Ltd.), 84 mL of 50% potassium hydroxide aqueous solution, and 423 mL of toluene were added and the resultant mixture was stirred. An inside of a reaction system was kept at 20 to 25° C. in a water bath, and 397.5 g (7.5 equivalents) of acrylonitrile was added dropwise over 2 hours. After the dropwise addition, the resultant mixture was stirred for 1.5 hours, and then 540 mL of toluene was added to the mixture, the reaction mixture was transferred to a separating funnel, and an aqueous layer was removed. The remaining organic layer was dried over magnesium sulfate, and then subjected to Celite filtration, a solvent was distilled off under reduced pressure, and thus an intermediate (B) was obtained. The obtained material was analyzed by $^1$H NMR and MS, and the analytical results showed a satisfactory agreement with those of a known material. Therefore, the material was used for the next reduction reaction without further purification.

(Second Step)

In a 1 L volume autoclave, 24 g of intermediate (B), 48 g of Co catalyst (Raney Cobalt 2700, made by W. R. Grace & Co.), and 600 mL of solution (25% aqueous ammonia:methanol=1:1) were put, the resultant mixture was suspended, and a reaction vessel was sealed. Hydrogen at 10 MPa was introduced into the reaction vessel, and a reaction was allowed at a reaction temperature of 25° C. for 16 hours.

Disappearance of the raw materials was confirmed by means of $^1$H NMR, the reaction mixture was subjected to Celite filtration, and the Celite filter was washed with methanol several times. A solvent was distilled off from the filtrate under reduced pressure, and thus an intermediate (C) was obtained. The material obtained was used for the next reaction without further purification.

(Third Step)

To a 2 L volume three-necked flask equipped with a stirrer, 29.2 g of intermediate (C), 48.48 g (4.8 equivalents) of triethylamine, and 1 L of acetonitrile were added, and 55.87 g (4.4 equivalents) of 3-chloropropionic acid chloride was added dropwise over 2 hours in an ice bath, and then the resultant mixture was stirred at room temperature for 1 hour. Disappearance of the raw materials was confirmed by means of $^1$H-NMR, a solvent was distilled off from the reaction mixture under reduced pressure, and the resultant product was subjected to Celite filtration, and the solvent was again distilled off under reduced pressure. Finally, the resultant product was purified by means of column chromatography (ethyl acetate:methanol=4:1), and thus a white solid at normal temperature was obtained (yield: 36%).

The white solid obtained was identified by means of $^1$H-NMR, $^{13}$C-NMR, IR, and MS under the following measuring conditions. Identified data are shown in FIGS. 1 to 3, 4A and 4B.

Figure 1:
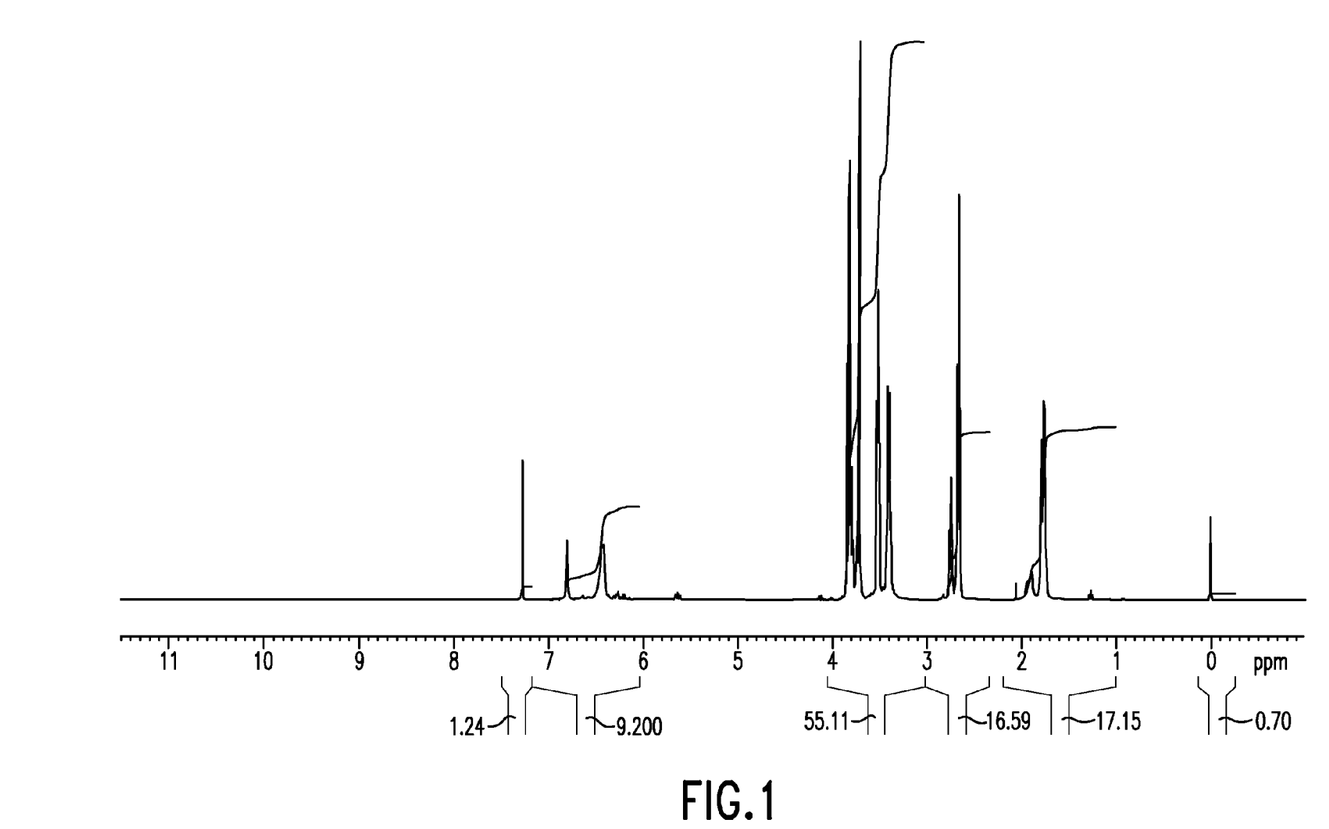
FIG. 1 is a $^1$H-NMR spectrum chart of the exemplified compound (1) synthesized in Example 1 as described later.

$^1$H-NMR

Figure 2:
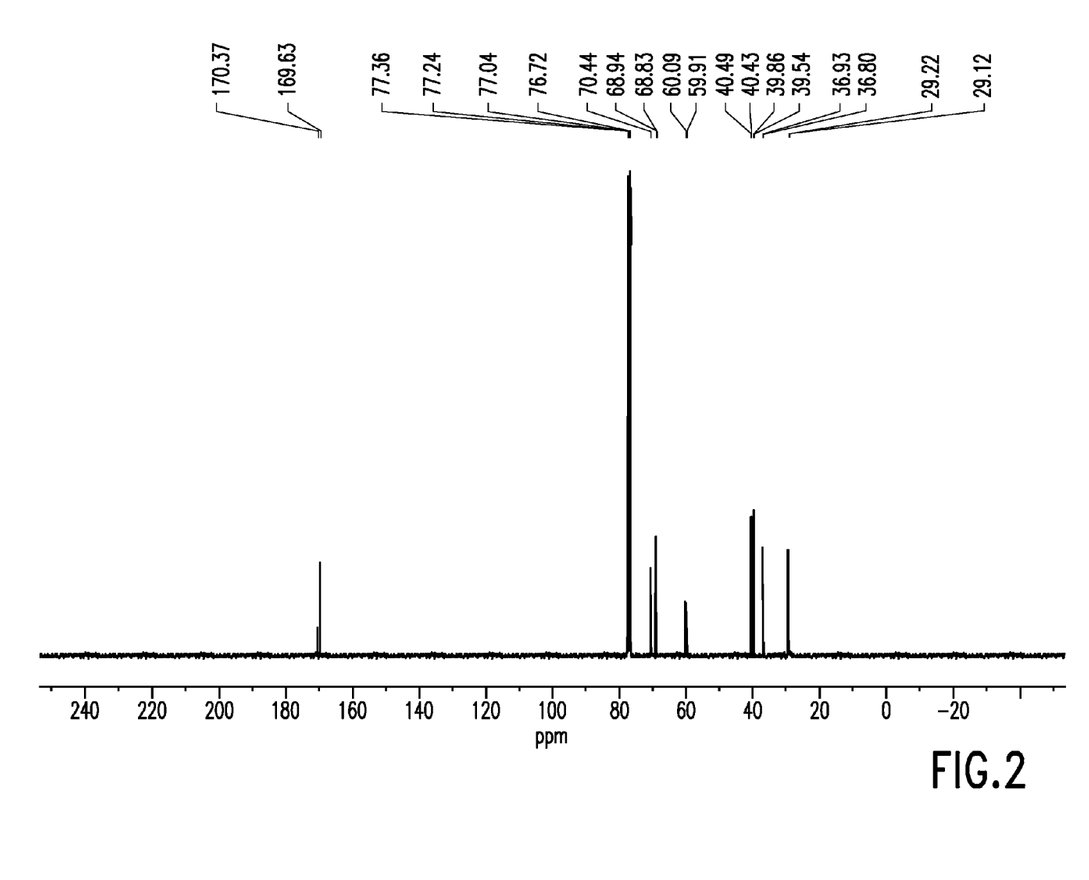
FIG. 2 is a $^{13}$C-NMR spectrum chart of the exemplified compound (1) synthesized in Example 1.

Solvent: deuterochloroform, Internal standard: TMS $^{13}$C-NMR

Solvent: deuterochloroform, Internal standard: TMS

IR

Figure 3:
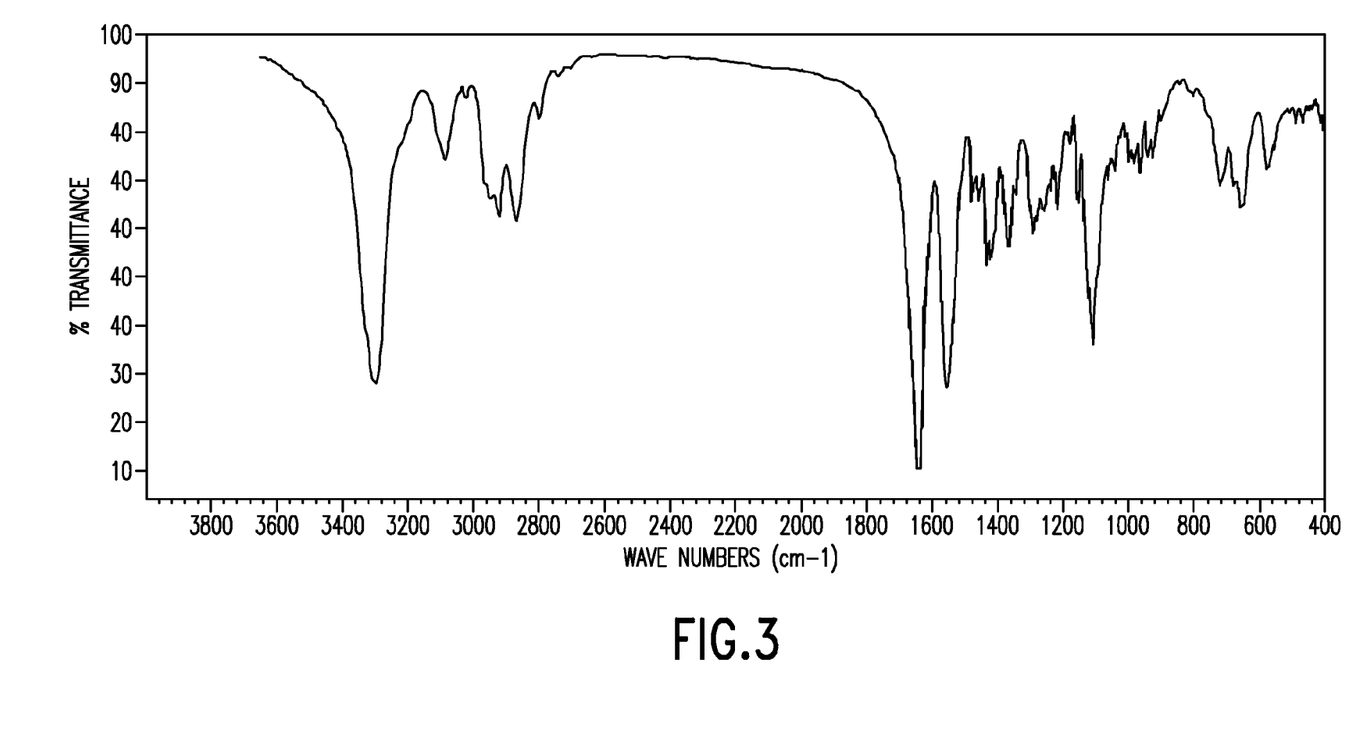
FIG. 3 is an IR spectrum chart of the exemplified compound (1) synthesized in Example 1.

A spectrum was measured according to a potassium bromide (KBr) tablet method, and converted into absorbance.

MS

Figure 4A:
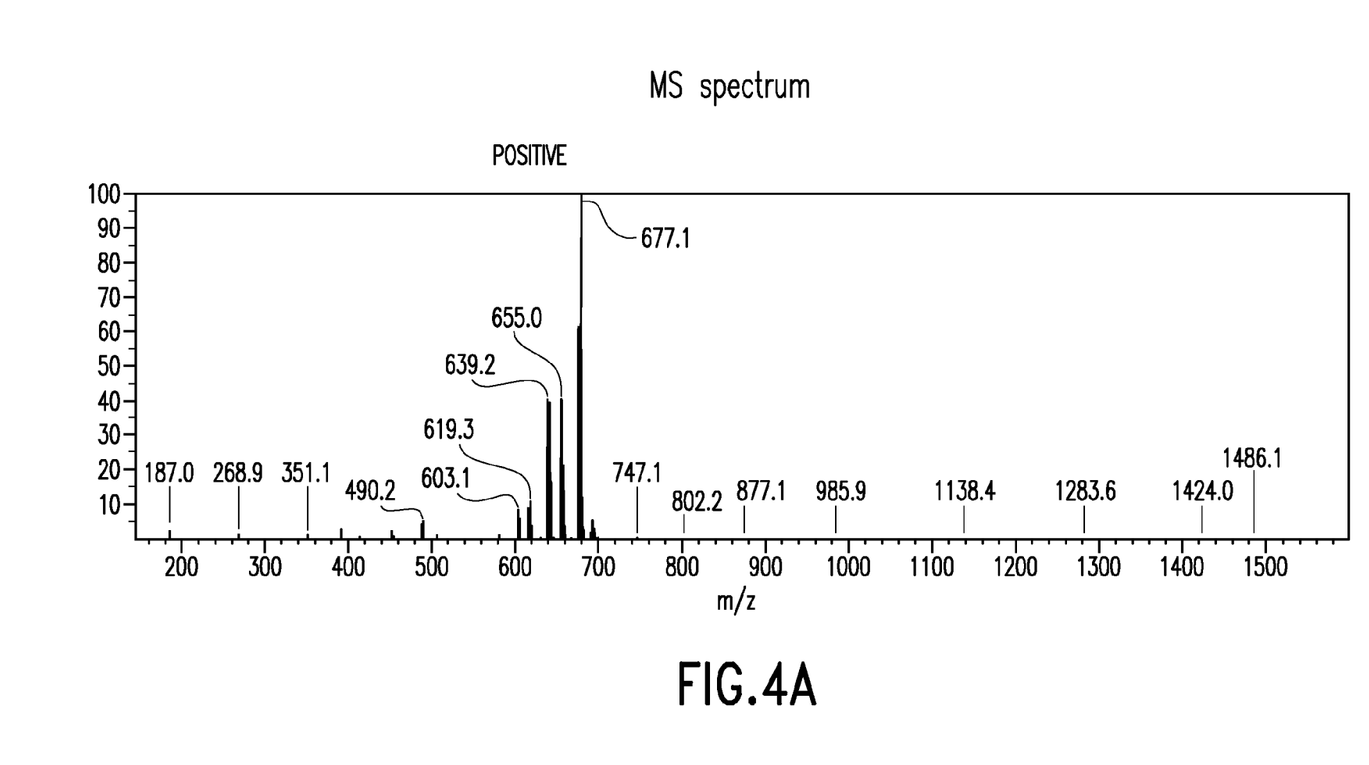
FIGS. 4A and 4B are MS spectrum charts of the exemplified compound (1) synthesized in Example 1.
Figure 4B:
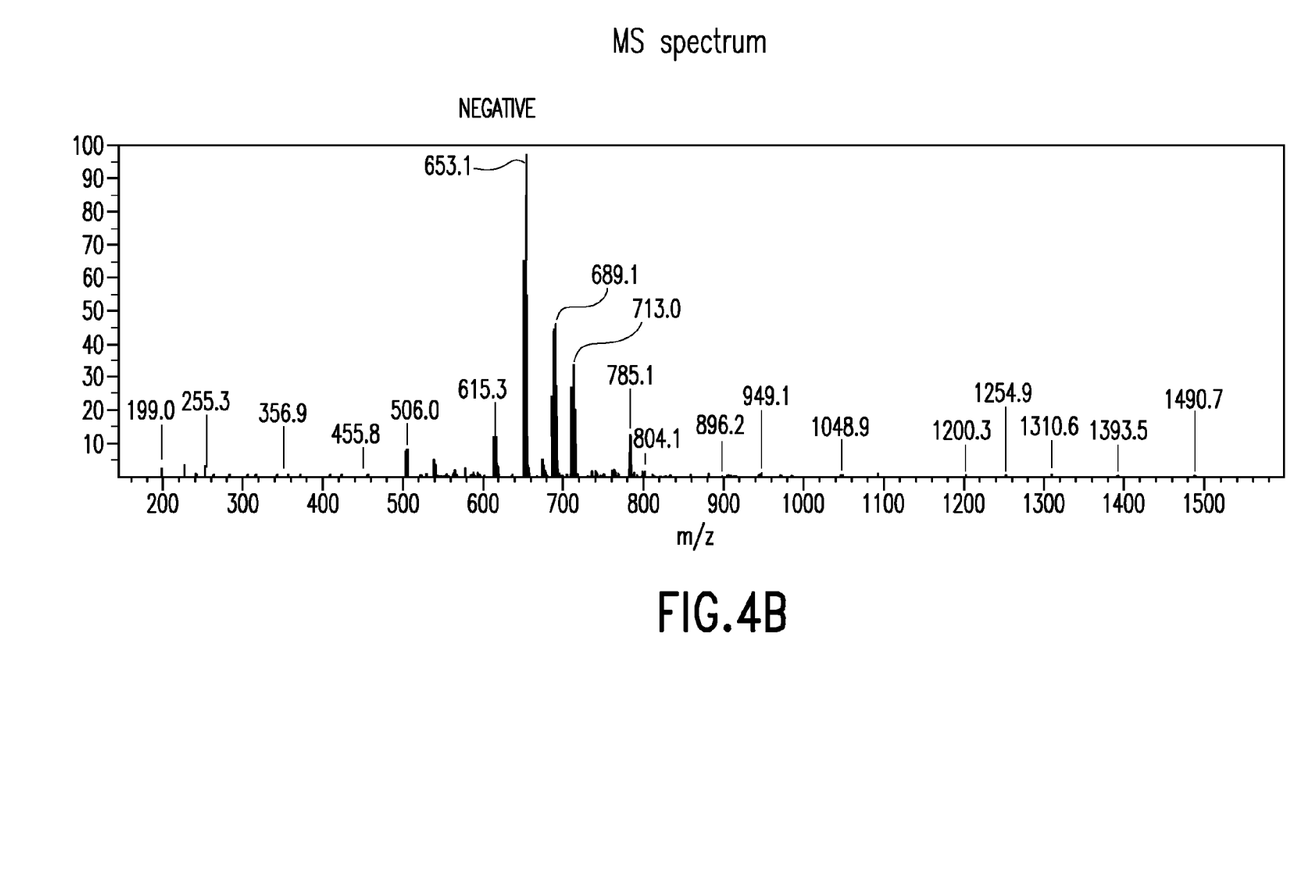

Solvent: MeOH/H$_2$O=9/1, 10 mM CH$_3$COONH$_4$

As a result of the above identification, the white solid was confirmed to have a structure of the exemplified compound (1).

Reference Example

Derivation of Acrylamide Compound from Exemplified Compound (1), and Evaluation of Hardening Properties of the Acrylamide Compound 1. Synthesis of Acrylamide Compound from Exemplified Compound (1)

An acrylamide compound (A1) was obtained by allowing a base to act on the exemplified compound (1) obtained in Example 1 according to the method as described in Russian Journal of General Chemistry, 2005, Vol. 75, No. 6, pp. 915-922, and U.S. Pat. No. 4,914,225, or according to a method equivalent thereto.

Acrylamide compound (A1)

2. Evaluation of Hardening Properties of Acrylamide Compound (A1)

The hardening properties (thermosetting properties) of the acrylamide compound (A1) obtained were evaluated according to the following procedures.

[Evaluation of Hardening Properties]

A sample solution containing the acrylamide compound (A1), a radical polymerization initiator, and an organic solvent was prepared and applied onto a copper plate, and then this was heated, and progress of radical polymerization and a sense of touch before and after heating were evaluated. In addition, the progress of radical polymerization was confirmed by a thermal decrease of a peak at 806 cm$^{-1}$ arising from an acrylic group by using FT-IR (VARIAN 3100 FT-IR (trade name), made by Varian, Inc.). The details are shown below.

A sample liquid 1A for evaluation was prepared by dissolving 250 mg of acrylamide compound (A1) and 25 mg of azobisisobutyronitril (AIBN) as the radical polymerization initiator in 1 mL of methanol. Then, 10 µL of this sample liquid 1A for evaluation was measured, and applied onto the copper plate.

The copper plate onto which the sample liquid was applied was measured by means of FT-IR, and the peak at 806 cm$^{-1}$ arising from the acrylic group was confirmed. Then, the copper plate was heated in an oven at 100° C. for 1 hour under a nitrogen atmosphere. When the copper plate after heating was again measured by means of FT-IR, the peak at 806 cm$^{-1}$ arising from the acrylic group decreased. From this result, the progress of radical polymerization of acrylamide compound (A1) was confirmed.

Furthermore, when the sense of touch before and after heating was evaluated, no stickiness was felt on the sample plate after heating when the sample plate was touched, and no change was felt when the sample plate was rubbed with a ball of a finger, as compared with the sense before rubbing. These results show a fact that the sample liquid applied onto the copper plate was hardened by heating.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2012-065144 filed in Japan on Mar. 22, 2012, which is entirely herein incorporated by reference.

What is claimed is:

1. A compound represented by formula (II):

Formula (II)

wherein, in formula (II), R represents a hydrogen atom or an alkyl group having 1 to 4 carbon atom(s); Ra represents a hydrogen atom, an alkyl group, an aryl group, or a heterocyclic group; X represents a halogen atom, or an alkyl- or aryl-sulfonyloxy group; L represents —O—, an alkylene group, or a divalent linking group obtained by combining these groups; Rb represents a hydrogen atom, an alkyl group, or -L-N(Ra)—C(=O)—CH(R)—CH$_2$—X; and a plurality of Rs, Ras, Xs, and Ls may be the same or different from each other, respectively.

2. The compound according to claim 1, wherein the compound represented by formula (II) is a compound represented by formula (III):

Formula (III)

wherein, in formula (III), R, Ra, X and L have the same meanings as those of formula (II).

3. The compound according to claim 1, wherein the compound represented by formula (II) is a compound represented by formula (1):

Formula (I)

wherein, in formula (I), $R^1$ represents a hydrogen atom or a methyl group; $X^1$ represents a halogen atom; $L^1$ represents an alkylene group having 1 to 6 carbon atom(s); $L^2$ represents a straight or branched alkylene group having 2 to 4 carbon atoms, and $L^2$ is linked to adjacent groups through at least two carbon atoms; k represents 2 or 3; m represents an integer of 0 to 6; and a plurality of $R^1$s, $L^1$s, $L^2$s, $X^1$s, ks and ms may be the same or different from each other, respectively.

* * * * *